United States Patent [19]
Reid et al.

[11] 4,410,753
[45] Oct. 18, 1983

[54] PROCESS AND CATALYST FOR SKELETAL ISOMERIZATION OF OLEFINS

[75] Inventors: Alexander J. Reid, Feasterville; Kenneth R. Olson, Wynnewood, both of Pa.

[73] Assignee: Publicker Industries, Inc., Greenwich, Conn.

[21] Appl. No.: 242,300

[22] Filed: Mar. 20, 1981

[51] Int. Cl.³ .................. C07C 5/30; B01J 26/06
[52] U.S. Cl. .................... 585/671; 502/231
[58] Field of Search .............. 252/442; 585/671

[56] References Cited

U.S. PATENT DOCUMENTS

| | | | |
|---|---|---|---|
| 2,209,492 | 7/1940 | Spicer | 23/223 |
| 2,361,508 | 10/1944 | Stahly et al. | 260/683.5 |
| 2,413,691 | 1/1947 | Crawford et al. | 260/683.5 |
| 3,140,925 | 7/1964 | Lindquist et al. | 252/441 |
| 3,166,542 | 1/1965 | Orzechowski et al. | 260/93.7 |
| 3,239,450 | 3/1966 | Lindquist et al. | 208/111 |
| 3,268,609 | 8/1966 | Nixon | 585/671 |
| 3,397,154 | 8/1968 | Talsma | 423/213.2 |
| 3,476,817 | 11/1969 | Vecchio | 570/169 |
| 3,498,927 | 3/1970 | Stiles | 252/451 |
| 3,513,109 | 5/1970 | Stiles | 423/213.2 |
| 3,758,418 | 9/1973 | Leonard et al. | 252/464 |
| 3,798,155 | 3/1974 | Wilhelm | 252/442 |
| 3,904,701 | 9/1975 | Schultz et al. | 570/166 |
| 3,907,715 | 9/1975 | Arai et al. | 252/465 |
| 3,950,270 | 4/1976 | Paynter et al. | 252/442 |
| 3,975,299 | 8/1976 | Crathorne et al. | 252/442 |
| 3,994,832 | 11/1976 | Antos | 252/464 |
| 4,036,903 | 7/1977 | Antos | 252/442 |
| 4,077,912 | 3/1978 | Dolhyj et al. | 427/215 |

OTHER PUBLICATIONS

V. Choudhary, Chemical Industry Developments, Incorporating C P & E, Jul. 1974, pp. 32-41.

Primary Examiner—Delbert E. Gantz
Assistant Examiner—Raymond Covington
Attorney, Agent, or Firm—Dann, Dorfman, Herrell and Skillman

[57] ABSTRACT

Straight chain olefinic hydrocarbons undergo skeletal isomerization upon contact at isomerizing temperatures with a catalyst in the form of a fluorine-activated-gamma-alumina including a minor amount of Bismuth for enhancing the effectiveness and prolonging the active life of the catalyst.

19 Claims, No Drawings

PROCESS AND CATALYST FOR SKELETAL ISOMERIZATION OF OLEFINS

The present invention relates to an improved fluorine-activated gamma-alumina catalyst, its method of preparation and its use in the catalytic isomerization of olefinic hydrocarbons. More specifically, this invention relates to the vapor phase skeletal isomerization of straight chain mono-olefins, especially straight chain 1-olefins, or mixtures thereof with straight chain 2-olefins. In particular, this invention is concerned with the conversion of straight chain butenes to isobutene.

As those skilled in the art will appreciate, the expression "skeletal isomerization", as used herein, refers to a rearrangement of the carbon structure of an olefinic hydrocarbon and is to be distinguished from double bond or geometric isomerization, which involves a shift of a hydrogen atom from one carbon to another in an olefin chain.

Fluorine-activated alumina is generally well known as a catalyst for effecting the skeletal isomerization of olefinic hydrocarbons. It has been reported that fluorinated gamma-alumina produces particularly good conversion rates with high selectivity, while exhibiting continued catalyst activity after several regenerations.

It has now been discovered, in accordance with the present invention, that the incorporation of a minor amount of bismuth in fluorine-treated gamma-alumina improves its effectiveness as a skeletal isomeritation catalyst. As compared with fluorine-activated gamma-alumina containing no modifier, the modified catalyst of the present invention gives enhanced conversion and selectivity and maintains a generally high level of activity for longer periods. As will be explained in greater detail hereinbelow, the improved catalyst of this invention may be prepared in a relatively simple and straightforward manner, using standard catalyst processing apparatus. The finished catalyst is employed in the usual way in carrying out vapor phase skeletal isomerization of straight chain olefinic hydrocarbons.

In accordance with one aspect of the present invention, there is provided an improved olefinic hydrocarbon skeletal isomerization catalyst comprising fluorine-treated gamma-alumina, which includes a sufficient amount of bismuth for enhancing the effectiveness and prolonging the active life of the fluorine-activated catalyst.

According to another aspect of this invention, there is provided a method for preparing the improved olefinic hydrocarbon skeletal isomerization catalyst, which comprises contacting gamma-alumina with a solution of a fluorinating agent to provide the requisite fluorine content in the finished catalyst; contacting the fluorinated gamma-alumina with a solution of a bismuth containing compound in a suitable solvent to provide the requisite bismuth content in the finished catalyst; and heating the fluorinated gamma-alumina, which includes bismuth, at elevated temperatures in an oxidizing atmosphere to provide the finished catalyst.

In accordance with yet another aspect of this invention, there is provided a process for converting normal olefinic hydrocarbons to their branched isomers, which process comprises contacting the olefinic hydrocarbon at isomerizing temperatures with the improved skeletal isomerization catalyst described herein.

As indicated above, this invention is characterized by the use of a catalyst comprising fluorine-activated gamma-alumina, which includes a minor amount of bismuth. The improved results noted above are readily achieved using a fluorine-activated catalyst containing from about 1.0% to about 10.0% by weight of bismuth. When the bismuth content of the catalyst is reduced below 1.0 weight %, the above noted improvement in conversion, selectivity and prolongation of catalyst life is not observed to any appreciable degree, whereas a bismuth content in excess of 10.0 weight % does not produce a commensurate improvement in the aforesaid catalyst properties, and thus is not cost effective. The fluorine content of the fluorine-activated gamma-alumina is preferably between about 0.5% and about 2.0% by weight. A fluorine content of lower than 0.5 weight % gives an unsatisfactory catalyst, while a flurorine content higher than about 2.0 weight % tends to increase the production of by-products, thus reducing the selectivity of the catalyst.

The gamma-alumina used in the practice of this invention may take various forms. Gamma-alumina spheres or pellets having a nominal diameter of $\frac{1}{8}$ inch have proved to be satisfactory.

Fluorine activation or impregnation of the gamma-alumina is carried out by contacting the gamma-alumina with a solution of a fluorinating agent, using techniques well known in the art. The fluorinating agent may be hydrogen fluoride or any substance which is capable of forming hydrogen fluoride upon decomposition, such as ammonium bifluoride, fluorine gas or a fluorocarbon. When using fluorine gas or fluorocarbons as the florinating agent, the hydrogen required for hydrogen fluoride formation may be supplied by hydroxide groups on the gamma-alumina, or by moisture or other hydrogen-containing materials associated with the gamma-alumina. Fluoborates and fluosilicates may also be used as the fluorinating agent. The presence of the boron or silicon in the finished catalyst does not have any appreciable effect on the improved properties thereof.

The impregnation of the gamma-alumina with fluorine may be conveniently carried out by forming a slurry of the gamma-alumina in a solution of the fluorinating agent, the amount of fluorinating agent used being calculated to provide the aforementioned florine content in the finished catalyst, i.e., from about 0.5 weight percent to about 2.0 weight percent. The slurry is thereafter heated at about 500° C. for a period of time sufficient to dry the fluorine-activated gamma-alumina and decompose and volatilize any undesirable compounds present on the gamma-alumina as a result of the fluorinating treatment. A heating period of about two hours is normally sufficient for this purpose.

Any bismuth-containing compound that is soluble in water or an organic solvent, such as alcohols, ethers or hydrocarbons, may be used to impregnate the fluorine-activated gamma-alumina. Suitable bismuth containing compounds include bismuth nitrate, bismuth tartrate, and bismuth ammonium citrate. Of these, bismuth nitrate is preferred because of its availability and relative low coat and ease of handling. The organic solvent selected to apply the bismuth-containing compound to the fluorine-treated gamma-alumina should be a solvent which can be evaporated without having to subject the catalyst to extreme heat. Solvents which have a boiling point below 300° C. or which readily decompose upon heating in the presence of oxygen are preferred. Satisfactory results have been obtained using a solution of bismuth nitrate in ethylene glycol, diethylene glycol, propylene, butylene glycol or mixtures or mixtures thereof. The concentration of the solution must be appropriate to provide a bismuth content of from about 1.0 percent to about 10.0 percent by weight in the finished catalyst. For example, if a catalyst containing 3 weight percent of bismuth is desired, bismuth nitrate is dissolved in just enough solvent to be absorbed in a reasonable length of time. The fluorine-activated alumina spheres are then mixed with the bismuth nitrate solution until all of the solution is taken up by the alumina spheres.

Due to the relatively high viscosity of ethylene glycol and diethylene glycol, the impregnation of the fluorine-treated gamma-alumina with a bismuth-containing compound dissolved in these solvents is a relatively slow process, which may suitably be carried out in a commercial tumbling mixer.

As the final step in preparing the catalyst, the fluorine-activated gamma-alumina including the bismuth-containing compound is heated at a temperature between 400° C. to 600° C. in the presence of oxygen, e.g., air, for a time sufficient to drive off the solvent and oxidize the bismuth-containing compound, thus providing the finished composite catalyst.

Although the form of the bismuth contained in the finished catalyst has not been accurately characterized, it is believed to be bismuth trioxide ($Bi_2O_3$).

While the above described procedure for the preparation of the catalyst involved fluorination of the gamma-alumina followed by impregnation with a bismuth-containing compound, the same catalyst will be obtained if these steps are carried out in reverse order. It should be noted, however, that the two steps of the procedure cannot be carried out simultaneously, for dissolution of the fluorinating agent and the bismuth containing compound in the same solvent will form an insoluble precipitate.

It should be understood that the fluorine and bismuth contents of the catalyst referred to herein are the theoretical content calculated from the quantity of the respective fluorinating agent and bismuth impregnating agent added to the gamma-alumina during preparation of the catalyst.

In carrying out the skeletal isomerization process of the present invention, a straight chain olefinic hydrocarbon is contacted at isomerization temperatures with the modified fluorine-activated gamma-alumina catalyst under the conditions described hereinbelow.

The preferred temperature for isomerization is between about 350° C. to about 450° C. Increasing the temperature beyond 450° C. tends to reduce selectivity. The process is conveniently carried out at or below atmospheric pressure, although super-atmospheric pressure as high as 30 psig. may be employed, if desired. However, operation under super-atmospheric pressure appears to increase side reactions. The olefin feed may be introduced into the reactor undiluted, or with a diluent gas, such as nitrogen. In the latter case, the partial pressure of olefin in the feed may be as low as 0.1 atm. The space velocity of the olefin feed may be in the range from about 3 to about 20 vol./vol./min.

The catalyst must be periodically regenerated to remove any carbonaceous material that is deposited thereon during operation of the process. Such deposits reduce the activity of the catalyst. Regeneration entails periodically interrupting the isobutene production, and passing an oxygen-containing gas over the catalyst to remove any carbonaceous material that may have been deposited thereon. Care must be taken to prevent the temperature of the catalyst from exceeding 700° C. during regeneration in order to avoid damaging the catalyst.

Although regneration does not result in any appreciable loss of catalyst activity, the activity of the catalyst will gradually be diminished after continued operation for long periods, requiring reactivation with a suitable gaseous fluorinating agent after one or more regenerations to restore the catalyst to its original activity. Although the reactivation is performed periodically, the period of time between reactivations may be considerably longer than the period between regenerations.

The invention will be further understood by reference to following examples which set forth the results of experiments in which n-butenes were converted to isobutene using unmodified fluorine-activated gamma-alumina and the modified catalyst described above.

EXAMPLE 1

Gamma-alumina (approximately ⅛ inch white spheres) was activated by treating with ammonium bifluoride according to the fluorine activation procedure described hereinabove. The activated catalyst was determined to have a fluorine content of 0.8%, measured as fluorine. No bismuth-containing compound was incorporated in the fluorine-activated gamma-alumina.

This catalyst was used in a vapor phase skeletal isomerization of n-butenes carried out in a tubular fixed bed reactor under the following conditions:

Isomerization temperature: 370° C. (approx.);
Pressure: atmospheric
Butene feed: 96 percent mixed cis and trans 2-butenes.
Space velocity: 8 vol./vol./min.

After approximately 17 hours of operation it was determined that the fluorine activated gamma-alumina catalyst used in this example provided 24.5% conversion and 79.0% selectivity on the average.

EXAMPLE 2

Fluorine-activated gamma-alumina prepared in the manner described in Example 1 was impregnated with a slution of bismuth nitrate in ethylene glycol according to the procedure described hereinabove. The finished catalyst was determined to have a bismuth content of 3.0% by weight, measured as $Bi_2O_3$, and a fluorine content of 0.8% by weight, measured as fluorine.

This catalyst was used in the vapor phase skeletal isomerization of n-butenes under essentially the same conditions as those employed in Example 1.

After approximately 17 hours of operation it was determined that the catalyst of this example provided 29.0% conversion and 81.8% selectivity on the average.

In addition, satisfactory conversion and selectivity were still obtained after operating 48 hours using the modified catalyst of Example 2 without regeneration (24.5% conversion; 71.7% selectivity), whereas the unmodified catalyst of Example 1 ceased producing satisfactory results after only 28 hours of operating without regeneration of the catalyst.

The foregoing examples demonstrate that the bismuth containing catalyst of the present invention is more effective and has a longer life than the fluorine-actived gamma-alumina catalyst of the prior art.

Under carefully controlled operating conditions conversion rates as high as 30 to 35% with 80 to 85% selectivity should be obtainable in accordance with the practice of the present invention.

Similar results may be obtained by substituting 1- and 2-pentenes, 1- and 2-hexenes or higher alkene homologs for the straight chain butenes in the foregoing examples.

The branched chain olefins produced in accordance with the present invention have a wide variety of utilities. For example, isobutene may be converted to methyl-t-butyl ether, a high octane gasoline additive, by methods well known to those skilled in the art. Branched chain olefins are also useful as starting materials in numerous chemical processes, e.g. as alkylating agents for the alkylation of aromatic hydrocarbons and phenols, and as monomers in polymerization and co-polymerization reactions with a wide range of catalysts to produce various rubber and plastic materials.

Those skilled in the art will appreciate that the description of the invention set forth hereinabove, including the foregoing examples, is merely illustrative and is capable of wide variation and modification without departing from the spirit and scope of the invention as defined in the appended claims.

We claim:

1. An olefin isomerization catalyst consisting essentially of fluorine-activated gamma-alumina having a fluorine content of from about 0.5 to about 2.0% by weight, and a sufficient amount of bismuth oxide for enhancing the effectiveness and prolonging the active life of said fluorine-activated catalyst.

2. An olefin isomerization catalyst consisting essentially of gamma-alumina, fluorine and bismuth oxide, said catalyst having a fluorine content from about 0.5% to about 2.0% by weight, and a bismuth content of from about 1.0% to about 10.0% by weight.

3. The olefin isomerization catalyst claimed in claim 2 wherein the bismuth contained in the catalyst is in the form of $Bi_2O_3$.

4. A process for converting a straight chain olefin to a branched chain olefin which comprises contacting said straight chain olefin at isomerizing temperatures with a catalyst comprising fluorine-activated gamma-alumina, said catalyst including a sufficient amount of bismuth for enhancing the effectiveness and prolonging the active life of said fluorine-activated catalyst.

5. The process claimed in claim 4 wherein the catalyst contains from about 1.0% to about 10.0% by weight of bismuth and from about 0.5% to about 2.0% by weight of fluorine.

6. The process claimed in claim 4 wherein the bismuth contained in the catalyst is in the form of $Bi_2O_3$.

7. The process claimed in claim 4 wherein straight chain butenes are converted to isobutene.

8. A process for converting a straight chain olefin to a branched chain olefin which comprises contacting said straight chain olefin at isomerizing temperatures with a catalyst consisting essentially of gamma-alumina, fluorine and bismuth oxide, said catalyst having a fluorine content of from about 0.5% to about 2.0% by weight, and a bismuth content of from about 1.0% to about 10.0% by weight.

9. The process claimed in claim 8 wherein the bismuth contained in the catalyst is in the form of $Bi_2O_3$.

10. The process claimed in claim 8 wherein straight chain butenes are converted to isobutene.

11. The process claimed in claim 8 wherein the isomerization temperature is from about 350° C. to about 450° C.

12. A process for converting a straight chain olefin to a branched chain olefin which comprises contacting said straight chain olefin at a space velocity of from about 3 to about 20 vol./vol./min. and at isomerizing temperatures with a catalyst consisting essentially of gamma-alumina having a fluorine content of from about 0.5% to about 2.0% by weight, and from about 1.0% to 10.0% by weight of bismuth.

13. The process claimed in claim 12 wherein the bismuth present in said catalyst is bismuth oxide.

14. The process claimed in claim 13 wherein straight chain butenes are converted to isobutenes.

15. A process for converting a straight chain olefin to produce isobutene which comprises contacting said straight chain olefin at a space velocity of from about 3 to about 20 vol./vol./min. and at a temperature from about 350° C. to about 450° C. with a catalyst consisting essentially of gamma-alumina having a fluorine content of from about 0.5% to about 2.0% by weight, and from about 1.0% to 10.0% by weight of bismuth; and periodically interrupting isobutene production while passing an oxygen-containing gas over the catalyst to remove carbonaceous material deposited thereon, and thereby regenerate the catalyst.

16. The process claimed in claim 15 wherein the bismuth present in said catalyst is bismuth oxide.

17. The process claimed in claim 16 wherein straight chain butenes are converted to isobutenes.

18. The process claimed in claim 15 which includes the step of passing a gaseous fluorinating agent through the catalyst after one or more regenerations to reactivate the catalyst.

19. The process claimed in claim 18 wherein the fluorinating agent used for catalyst reactivation is selected from the group consisting of hydrogen fluoride, fluorine, or a fluorocarbon.

* * * * *

UNITED STATES PATENT AND TRADEMARK OFFICE
CERTIFICATE OF CORRECTION

PATENT NO. : 4,410,753

DATED : October 18, 1983

INVENTOR(S) : Reid et al.

It is certified that error appears in the above-identified patent and that said Letters Patent is hereby corrected as shown below:

Column 2, line 59, "coat" should be --cost--.

Column 2, line 68, after "propylene" --glycol-- should be inserted; and "or mixtures" (first occurrence) should be deleted.

Column 4, line 43, "sultion" should be --solution--.

Signed and Sealed this

Third Day of January 1984

[SEAL]

Attest:

GERALD J. MOSSINGHOFF

*Attesting Officer*     *Commissioner of Patents and Trademarks*